United States Patent [19]

Görög et al.

[11] Patent Number: 4,511,714
[45] Date of Patent: Apr. 16, 1985

[54] HERBICIDAL ANTIDOTE COMPOSITIONS

[75] Inventors: Katalin Görög; Erzébet Dudar; Iván Gárdi; Mária Kocsis; Sándor Gaál; Márta Tasnádi, all of Budapest, Hungary

[73] Assignee: Nitrokemia Ipartelepek, Fuzfogyartelep, Hungary

[21] Appl. No.: 476,240

[22] Filed: Mar. 17, 1983

Related U.S. Application Data

[63] Continuation-in-part of Ser. No. 354,070, Mar. 2, 1982, , which is a continuation of Ser. No. 181,741, Aug. 26, 1980.

[51] Int. Cl.$^3$ .............................. C07D 263/00
[52] U.S. Cl. ............................ 548/215; 71/93
[58] Field of Search ........................... 548/215

[56] References Cited

U.S. PATENT DOCUMENTS

| | | | |
|---|---|---|---|
| 3,160,634 | 12/1964 | Hodge | 548/215 |
| 3,218,328 | 11/1965 | Shapiro et al. | 548/215 |
| 4,021,224 | 5/1977 | Pallos et al. | 548/215 |
| 4,174,450 | 11/1979 | Bodor | 548/215 |

FOREIGN PATENT DOCUMENTS 1445952 1/1969 Fed. Rep. of Germany ...... 548/215

Primary Examiner—Paul J. Killos
Attorney, Agent, or Firm—Toren, McGeady and Stanger

[57] ABSTRACT

The invention concerns herbicidal compositions comprising an active herbicidal compound of the thiolcarbamate, substituted urea, substituted triazine or chloroacetanilide type or optional mixtures thereof, and an antidote therefor having the general formula I

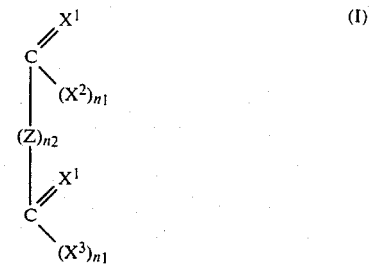

wherein
$X^1$ represents oxygen, sulphur or nitrogen;
$n_1$ is 0 or 1;
$X^2$ and $X^3$ which may be the same or different, each represent hydroxyl, alkoxy having 1 to 5 carbon atoms, alkenyloxy having 2 to 5 carbon atoms, amino, alkylamino having 1 to 4 carbon atoms or 2,2-dimethyl-1,3-oxazolidinyl;
$n_2$ is 0 or 1; and
Z represents alkylene having 1 to 4 carbon atoms, alkenylene having 2 to 4 carbon atoms, phenylene, tetrahydrophenylene, hexahydrophenylene or endomethylene-tetrahydrophenylene.

4 Claims, No Drawings

HERBICIDAL ANTIDOTE COMPOSITIONS

CROSS-REFERENCE TO RELATED APPLICATIONS

This application is a continuation-in-part of copending application Ser. No. 354,070, filed Mar. 2, 1982, which, in turn, is a continuation of application Ser. No. 181,741, filed Aug. 26, 1980.

This invention relates to herbicidal antidote compositions.

It is well known that many of the commercially available herbicides may cause serious injuries also to the cultivated plants to be protected. This phytotoxic effect is a function of the dose employed and strongly depends on the weather conditions. Some known herbicides are strongly phytotoxic already when used in the effective doses to control undesired plant growth. Many attempts have been made to overcome this problem.

According to the Hungarian Pat. No. 165 736 N,N-disubstituted dichloroacetamides are added to known herbicides in an amount of 0.0001 to 30% by weight. These N,N-disubstituted dichloroacetamides are said to be especially successful in combination with herbicides of the thiolcarbamate, urea and triazine type.

U.S. Pat. No. 3,131,509 discloses the use of 1,8-naphthalic acid and derivatives thereof (anhydrides, esters, amide etc.) to decrease the phytotoxicity of known herbicides.

A considerable research activity is carried out to find further compounds called "antidotes" which reduce the phytotoxic effect of known herbicides to an even lower level.

It has been found that plants may be protected against injury by active herbicidal compounds, as hereinafter defined, and/or the tolerance of the plants to such compounds may be substantially increased by the use of certain antidote compounds.

The present invention provides a herbicidal composition comprising an active herbicidal compound, as hereinafter defined, and an antidote therefor corresponding to the general formula I

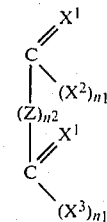

wherein $X^1$ represents oxygen, sulphur or nitrogen;

$n_1$ is 0 or 1;

$X^2$ and $X^3$ which may be the same or different, each represent hydroxyl, alkoxy having 1 to 5 carbon atoms, alkenyloxy having 2 to 5 carbon atoms, amino, alkylamino having 1 to 4 carbon atoms or 2,2-dimethyl-1,3-oxazolidinyl;

$n_2$ is 0 or 1; and

Z represents alkylene having 1 to 4 carbon atoms, alkylene having 2 to 4 carbon atoms, phenylene, tetrahydrophenylene, hexahydrophenylene or endomethylene-tetrahydrophenylene.

In the above description the term alkoxy having 1 to 5 carbon atoms preferably includes alkoxy groups having 1 to 4 carbon atoms, more preferably methoxy, ethoxy or butoxy groups. The term alkenyloxy having 2 to 5 carbon atoms preferably includes allyloxy group.

The present invention also provides a method of controlling undesired plant growth comprising applying to the plants a herbicidally effective amount of a composition according to the invention.

The present invention further provides a method of protecting a plant crop from injury due to an active herbicidal compound which involves applying to the soil prior to the use of a herbicidal compound or simultaneously with that a non-phytotoxic, antidotally effective amount of a compound corresponding to the above-defined general formula (I).

The terms antidote or antidotal amount are meant to describe that effect which tends to counteract the normal injurious herbicidal response that the herbicide might otherwise produce.

The antidotes according to the invention are generally used in an amount of 1 to 50% by weight calculated for the weight of the acive herbicidal compound.

Some typical representatives of the antidotes according to the invention (compounds of the general formula /I/) together with their physical constants are listed in the following Table I.

TABLE I

| No. | $n_1$ | Z | $X^1$ | $n_2$ | $X^2$ | $X^3$ | Compound | Phys. const. (M.p., B.p.) °C. |
|---|---|---|---|---|---|---|---|---|
| 1 | 1 | — | O | 1 | amino-, | amino-, | oxalic acid diamide | M.p.: 419 (decomp.) |
| 2 | 1 | — | O | 1 | ethoxy-, | amino-, | oxalic acid monoethylester amide | M.p.: 110 |
| 3 | 1 | methylene | O | 1 | ethoxy-, | ethoxy-, | malonic acid diethylester | B.p.: 198–199 |
| 4 | 1 | ethylene | O | 1 | amino-, | amino-, | succinic acid diamide | M.p.: 268–270 |
| 5 | 1 | butylene | O | 1 | methoxy-, | methoxy-, | adipinic acid dimethylester | M.p.: 10,3 |
| 6 | 1 | butylene | O | 1 | ethoxy-, | ethoxy-, | adipinic acid diethylester | B.p.: 239–241 |
| 7 | 1 | butylene | O | 1 | amino-, | amino-, | adipinic acid diamide | M.p.: 223 |
| 8 | 1 | vinylene | O | 1 | methoxy-, | methoxy-, | maleinic acid dimethylester | B.p.: 205 |
| 9 | 1 | vinylene | O | 1 | ethoxy-, | ethoxy-, | maleinic acid diethylester | B.p.: 225 |
| 10 | 1 | phenylene | O | 1 | hydroxyl-, | hydroxyl-, | isophthalic acid | M.p.: 348 |
| 11 | 1 | phenylene | O | 1 | hydroxyl-, | hydroxyl-, | terephthalic acid | sublimation |
| 12 | 1 | phenylene | O | 1 | methoxy-, | methoxy-, | phthalic acid dimethylester | B.p.: 283,8 |
| 13 | 1 | phenylene | O | 1 | ethoxy-, | ethoxy-, | phthalic acid diethylester | B.p.: 298 |
| 14 | 1 | phenylene | O | 1 | butoxy-, | butoxy-, | phthalic acid dibutylester | B.p.: 340 |
| 15 | 1 | phenylene | O | 1 | allyloxy-, | allyloxy-, | phthalic acid diallyester | B.p.: 120–130 |

TABLE I-continued

| No. | $n_1$ | Z | $X^1$ | $n_2$ | $X^2$ | $X^3$ | Compound | Phys. const. (M.p., B.p.) °C. |
|---|---|---|---|---|---|---|---|---|
| 16 | 1 | endo-methylene tetrahydro-phenylene | O | 1 | hydroxyl-, | hydroxyl-, | endo-methylene-tetrahydro-phthalic acid | M.p.: 177-179 |
| 17 | 1 | phenylene | O | 1 | amino-, | amino-, | isophthalic acid amide | M.p.: 280 |
| 18 | 1 | phenylene | O | 1 | amino-, | amino-, | terephthalic acid amide | M.p.: 219-220 |
| 19 | 1 | phenylene | O | 1 | 2,2-dimethyl-1,3-oxazolidinyl | 2,2-dimethyl-1,3-oxazolidinyl | phthalic acid-bis-(2,2-dimethyl-1,3-oxazolidine | M.p.: 130-132 |
| 20 | 1 | phenylene | O | 1 | 2,2-dimethyl-1,3-oxazolidinyl | 2,2-dimethyl-1,3-oxazolidinyl | isophthalic acid-bis-(2,2-dimethyl-1,3-oxazolidine | M.p.: 55 (decomp.) |
| 21 | 1 | phenylene | O | 1 | 2,2-dimethyl-1,3-oxazolidine | 2,2-dimethyl-1,3-oxazolidine | terephthalic acid-bis-(2,2-dimethyl-1,3-oxazolidine) | M.p.: 204-207 |
| 22 | 1 | phenylene | O | 1 | hydroxyl-, | 2,2-dimethyl-1,3-oxazolidinyl | terephthaloyl-2,2-dimethyl-1,3-oxazolidine | M.p.: 318-320 |
| 23 | 0 | phenylene | N | 1 | — | — | phthalic acid-dinitrile | M.p.: 137-140 |
| 24 | 0 | phenylene | N | 1 | — | — | terephthalic acid dinitrile | M.p.: 216-222 |
| 25 | 1 | phenylene | S | 1 | amino-, | amino-, | isophthalic acid-dithion-amide | M.p.: 214 |
| 26 | 1 | phenylene | S | 1 | amino-, | amino-, | terephthalic acid-dithion-amide | M.p.: 227 |

The antidotes of the general formul I have been found effective in combination with thiolcarbamates, substituted ureas, substituted triazines and chloroacetanilides having herbicidal activity.

The majority of the antidotes used according to the present invention can be prepared by methods known in the art.

The preparation of endo-methylene-tetrahydrophthalic acid (compound No. 16) by reacting maleic acid with cyclopentadiene with a yield of 94% is for example described in Czechoslovakian Pat. No. 86,914.

Terephthalic acid (Compound No. 11) can for example be prepared according to Organic Syntheses Coll. Vol. III. 791 by oxidizing p-methylacetophenone with a yield of 84 to 88%.

According to U.S. Pat. No. 2,856,424 isophthalic acid (Compound No. 10) can for instance be prepared by oxidizing m-xylene.

Dicarboxylic acid esters Nos. 3, 5, 6, 8, 9, 12, 13, 14 and 15 can be prepared by reacting a corresponding dicarboxylic acid anhydride with a suitable alcohol (see British Pat. No. 645,218).

Dicarboxylic acid amides Nos. 1, 4, 7, 17 and 18 can be prepared according to U.S. Pat. No. 2,820,021 by reacting a dicarboxylic acid dichloride with a corresponding amine. Thioacid amides (Compounds Nos. 25 and 26) can be obtained in an analogeous way starting from the corresponding thiocarboxylic acids.

The preparation of new compounds Nos. 19, 20, 21 and 22 is illustrated by the following examples.

EXAMPLE 1

Preparation of phthalic acid bis-N,N-(2,2-dimethyl-1,3-oxazolidine)

Into a 250-ml. flask equipped with a stirrer, thermometer and a feed-way a solution of 10.1 g. (0.1 moles) of 2,2-dimethyl-1,3-oxazolidine in 80 ml. of benzene is added followed by a dropwise addition of a solution of 4.4 g. (0.11 moles) of sodium hydroxide in 15 ml. of water at 0° C., with continuous stirring. Thereafter a solution of 10.2 g. (0.05 moles) of phthalic acid dichloride in 20 ml. of benzene is added into the mixture portionwise, taking care that the temperature should not exceed 6° C. The reaction mixture is then stirred at room temperature for two hours and is allowed to stand overnight. The two phases are separated, the benzene is dried and distilled off in vacuo. The remaining dense oil is digerated with petroleum ether and the crystalline product obtained is recrystallized from cyclohexanol. Melting point: 130° to 132° C.

Analysis: Calculated: C 65.04%; H 7.28%; N 8.43%; Found: C 65.02%; H 7.14%; N 8.73%.

Also the IR spectrum corresponds to the structure of title compound.

EXAMPLE 2

The preparation of terephthalic acid bis-N,N-(2,2-dimethyl-1,3-oxazolidine)

Into a 500-ml. flask equipped with a stirred, thermometer and a feed-way a solution of 10.1 g. (0.1 moles) of 2,2-dimethyl-1,3-oxazolidine in 80 ml. of benzene is added followed by a dropwise addition of a solution of 4.4 g. (0.11 moles) of sodium hydroxide in 15 ml. of water at 0° C., with continuous stirring. Thereafter a solution of 10.2 g. (0.05 moles) of terephthalic acid dichloride in 140 ml. of benzene is added into the mixture portionwise, taking care that the temperature should not exceed 6° C. The reaction mixture is then stirred for two hours and the product is precipitated by addition of hexane. The precipitate is filtered off, washed with water and dried. Melting point: 197° to 201° C. The melting point of the product purified by recrystallization from absolute ethanol amounts to 207° C.

Analysis: Calculated: C 65.04%; H 7.28%; N 8.43%; Found: C 64.91%; H 7.30%; N 8.95%.

Also the IR spectrum corresponds to the structure of title compound.

EXAMPLE 3

The preparation of terephthaloyl-N-(2,2-dimethyl-1,3-oxazolidine)

Following the procedure described in the previous examples into a solution of 5.0 g. (0.05 moles) of 2,2-dimethyl-1,3-oxazolidine in 40 ml. of benzene 4.4 g. (0.11 moles) of sodium hydroxide and 15 ml. of water are added, whereupon the reaction mixture is treated with 10.2 g. (0.05 moles) of terephthalic acid dichloride. When the reaction terminates the pH of the reaction mixture is adjusted to 3. Benzene is distilled off, the residue is dissolved in acetone and precipitated with petroleum ether. The crystalline product obtained is filtered, washed with water and dried. Melting point: 318° to 320° C.

Analysis: Calculated: C 62.64%; H 6.07%; N 5.62%; Found: C 62.05%; H 6.00%; N 5.85%.

Also the IR spectrum corresponds to the structure of the title compound.

The compositions and compounds used according to the present invention may be used in any convenient form. Thus, the active herbicidal compounds and the antidotes may be formulated into emulsifiable concentrates, wettable powders, granulates, powders or any other convenient form. The compositions containing the herbicidal compound, antidote and conventional additives can be incorporated into the soil prior or after seeding. Alternatively, the active herbicidal compound and the antidote can be formulated separately and can be incorporated into the soil one after the other. According to a preferred embodiment the seeds are treated with a suitable formulation of an antidote of the general formula I prior to seeding and the suitably formulated herbicidal compound is incorporated into the soil prior or after seeding.

Compounds of the general formula I can be formulated in the same way as known active herbicidal compounds. As used herein, the term "active herbicidal compound" means active thiolcarbamates alone, active substituted ureas alone, active substituted triazines alone, active chloroacetanilides alone, or optional mixtures thereof.

The preparation of certain antidote formulations is illustrated by the following Examples 4 to 6.

EXAMPLE 4

Powder formulation containing isophthalic acid (Compound No. 10)

70 g. of isophthalic acid, 17 g. of kaolin, 8 g. of amorphous silicic acid (Ultrasil), 2.5 g. of fatty alcohol sulfonate and 2.5 g. of sulfite liquor powder are blended and ground in an air blast mill. The flotability of the powder obtained amounts to 97%.

EXAMPLE 5

Emulsifiable concentrate containing maleic acid dimethylester (Compound No. 8)

50 g. of maleic acid dimethylester and 5 g. of Emulsogen I 40 emulsifying agent are diluted to 100 ml. with isophoron. Before use the concentrate is diluted to the desired concentration with water.

EXAMPLE 6

Emulsifiable concentrate containing phthalic acid dimethylester (Compound No. 12)

50 g. of phthalic acid dimethylester and 5 g. of Emulsogen I 40 emulsifying agent are diluted to 100 ml. with xylene. Before use the concentrate is diluted to the desired concentration with water and the ready to use emulsion is applied to the soil by spraying.

The compositions according to the invention, which contain an active herbicidal compound, as hereinbefore defined, and an antidote of the general formula I were tested as described in Examples 7 to 13. In the examples Afalone=N-(3,4-chlorophenyl)-N'-methoxy-N'-methylurea;

Eptam=S-ethyl-N,N-dipropylthiolcarbamate;

Sencor=4-amino-6-tert.-butyl-3-methylthio-1,2,4-triazin-5-one;

Lasso=2-chloro-2',6'-diethyl-N-(methoxymethyl)-acetanilide.

EXAMPLE 7

The injurious effect of Afalone on sunflowers was tested. Simultaneously, it was examined how the tolerance of sunflowers to this herbicidal compound was increased by the use of the known antidote N,N-diallyl-2,2-dichloroacetamide and various compounds of the general formula I, respectively.

Tests were carried out on 10 m$^2$ plots with four repetitions. Afalone was used in each experiment as "Afalone 50 WP" in a dose of 5 kg./ha. Antidotes were applied parallel with Afalone as aqueous suspensions. Application was made by spraying.

On the control plots mechanical weed-killing was carried out. The green weight of the sunflowers cut from the treated plots was expressed in percents of the green weight of the sunflowers collected from the untreated (control) plots (100%). The results obtained are listed in the following Table 2:

TABLE 2

| Treatment | Dose (kg/ha) | | |
|---|---|---|---|
| | 0.5 | 1.0 | 2.0 |
| | green weight (%) | | |
| Afalone | 41 | 41 | 41 |
| Afalone + N,N—diallyl-2,2-dichloroacetamide | 48 | 51 | 57 |
| Afalone + Compound No. 11 | 52 | 67 | 80 |
| Afalone + Compound No. 15 | 52 | 78 | 87 |
| Afalone + Compound No. 18 | 67 | 78 | 95 |
| Afalone + Compound No. 21 | 68 | 76 | 98 |
| Control (mechanical weed-killing) | 100 | 100 | 100 |

The data reported in the above Table 2 clearly indicate that the herbicidal antidote compositions according to the invention (Afalone+a compound of the general formula I) showed a significantly lower phytotoxic effect than Afalone alone or Afalone in combination with N,N-diallyl-2,2-dichloroacetamide. When using the compositions according to the invention, especially those containing antidotes No. 18 and 21 the green weight of the sunflowers was nearly identical with the green weight of sunflowers collected from the control plot where mechanical weed-killing was performed.

EXAMPLE 8

The text procedure described in Example 7 was followed except that the sunflower seeds were treated with the formulations containing the antidote compounds prior to seeding and Afalone 50 WP was applied to the soil after seeding in a dose of 5 kg./ha. by spraying.

The injury reduction provided by the herbicide antidotes was even more expressed than in Example 7. The results tabulated in Table 3 show that the green weight of the sunflowers collected from the treated plots was practically identical with the green weight of the sunflowers collected from the control plots where mechanical weed-killing was carried out.

TABLE 3

| Treatment | Dose (kg./q.) | |
|---|---|---|
| | 0.5 | 1.0 |
| | green weight (%) | |
| Afalone | 41 | 41 |
| N,N—diallyl-2,2-dichloracetamide + Afalone | 62 | 71 |
| Compound No. 11 + Afalone | 78 | 95 |
| Compound No. 15 + Afalone | 68 | 82 |
| Compound No. 18 + Afalone | 70 | 98 |
| Compound No. 21 + Afalone | 79 | 99 |
| Control (mechanical weed-killing) | 100 | 100 |

EXAMPLE 9

The injurious effect of Eptam 6 E on maize was tested. Simultaneously, it was examined how the tolerance of maize to this herbicide was increased by the use of the known antidotes 1,8-naphthalic acid anhydride and N,N-diallyl-2,2-dichloroacetamide; and of 0.5, 1.0 and 2.0 kg./ha. doses of various antidotes of the general formula I, respectively. A combination of the herbicidal and the antidotes was applied to the soil as a tank-mix prior to seeding. Four repetitions were made.

The percentage results reported in Table 4 show the green weight of the maize collected from the treated plots expressed in percents of the green weight of the maize collected from the untreated (control) plots (100%), on which a mechanical weed-killing was performed.

TABLE 4

| Treatment | Dose (kg./ha.) | | |
|---|---|---|---|
| | 0.5 | 1.0 | 2.0 |
| | green weight (%) | | |
| Eptam | 48 | 48 | 48 |
| Eptam + 1,8-naphthalic acid anhydride | 60 | 64 | 70 |
| Eptam + N,N—diallyl-2,2-dichloroacetamide | 69 | 84 | 92 |
| Eptam + Compound No. 16 | 70 | 85 | 93 |
| Eptam + Compound No. 19 | 76 | 88 | 94 |
| Eptam + Compound No. 21 | 77 | 87 | 95 |
| Eptam + Compound No. 23 | 69 | 85 | 94 |
| Control (mechanical weed-killing) | 100 | 100 | 100 |

From the data obtained it can be concluded that the protection provided by the antidotes according to the invention is essentially better than the effect which can be achieved by using 1,8-naphthalic acid anhydride and slightly exceeds the protection obtained by N,N-diallyl-2,2-dichloroacetamide.

EXAMPLE 10

The injurious effect of Eptam on maize was tested. Simultaneously, it was tested how the tolerance of maize to this herbicide was increased by the use of the known herbicides 1,8-naphthalic acid anhydride and N,N-diallyl-2,2-dichloroacetamide, and of certain antidotes of the general formula I, respectively. 100 kg. of seeds of maize were treated with 0.25; 0.50 and 1.00 kg. doses of the above-mentioned antidotes by seed-dressing and maize was seeded into plots which had been treated with a 13 lit./ha. dose of Eptam 6 E herbicide composition. Four repetitions were made.

The results obtained are set forth in the following Table 5.

TABLE 5

| Treatment | Dose (kg./q.) | | |
|---|---|---|---|
| | 0.25 | 0.50 | 1.00 |
| | green weight (%) | | |
| Eptam | 48 | 48 | 48 |
| 1,8-naphthalic acid anhydride + Eptam | 68 | 70 | 78 |
| N,N—diallyl-2,2-dichloroacetamide + Eptam | 65 | 75 | 80 |
| Compound No. 16 + Eptam | 65 | 78 | 82 |
| Compound No. 19 + Eptam | 68 | 80 | 95 |
| Compound No. 21 + Eptam | 70 | 82 | 98 |
| Control (mechanical weed-killing) | 100 | 100 | 100 |

The data tabullated in Table 5 clearly show that seed-dressing carried out with the tested compounds of the general formula I provides a practically full protection against the injurious effect of Eptam.

EXAMPLE 11

The injurious effect of Sencor on soybeans was tested. Simultaneously, it was examined how the tolerance of soybeans to this herbicide was increased by the use of the known herbicides 1,8-naphthalic acid anhydride and N,N-diallyl-2,2-dichloroacetamide, and of certain antidotes according to the invention, respectively.

Tests were carried out on 10 m² plots with four repetitions. Sencor was used in each experiment in a dose of 1.5 kg./ha., while the antidotes were used in doses of 1.0 and 2.0 kg./ha. respectively. Both the herbicide and the antidotes were employed as aqueous suspensions.

Evaluation was performed as in the foregoing examples. On the control plots mechanical weed-killing was carried out.

The results obtained are shown in the following Table 6.

TABLE 6

| Treatment | Dose (kg./ha.) | |
|---|---|---|
| | 1.0 | 2.0 |
| | green weight (%) | |
| Sencor | 17 | 17 |
| Sencor + 1,8-naphthalic acid anhydride | 41 | 52 |
| Sencor + N,N—diallyl-2,2-dichloroacetamide | 21 | 26 |
| Sencor + Compound No. 10 | 51 | 66 |
| Sencor + Compound No. 11 | 56 | 68 |
| Sencor + Compound No. 19 | 58 | 81 |
| Control (mechanical weed-killing) | 100 | 100 |

From the data obtained it can be concluded that the antidotes according to the invention provide a considerable protection to soybeans against the injuries caused by Sencor, and their effect is significantly better than that of the known antidotes.

EXAMPLE 12

The injurious effect of Sencor on soybeans was tested. Simultaneously, it was examined how the tolerance of soybeans to this herbicide was increased by the use of the known antidotes 1,8-naphthalic acid anhydride and N,N-diallyl-2,2-dichloroacetamide and of certain compounds of the general formula I, respectively.

The seeds of soybeans were treated with doses of 0.25 and 0.50 kg./100 kg. of seeds of the antidotes by seed-dressing, and the herbicide (Sencor) was applied to the soil after seeding, in a dose of 1.5 kg./ha. by spraying.

Evaluation was made as described in the foregoing examples. The test results are set forth in the following Table 7.

TABLE 7

| Treatment | Dose (kg./q.) 0.25 green weight (%) | 0.5 |
|---|---|---|
| Sencor | 17 | 17 |
| 1,8-naphthalic acid anhydride + Sencor | 26 | 28 |
| N,N—diallyl-2,2-dichloroacetamide + Sencor | 70 | 82 |
| Compound No. 10 + Sencor | 69 | 87 |
| Compound No. 11 + Sencor | 68 | 78 |
| Compound No. 19 + Sencor | 72 | 95 |
| Control (mechanical weed-killing) | 100 | 100 |

From the results obtained the conclusion can be drawn that the antidotes according to the invention provide an even better protection when they are used by seed-dressing than as aqueous suspensions by spraying, for example in the case of Compound No. 19 practically full protection was obtained.

EXAMPLE 13

The injurious effect of Lasso on sorghum was tested. Simultaneously, it was examined how the tolerance of sorghum to this herbicide was increased by the use of the known antidote N,N-diallyl-2,2-dichloroacetamide and certain antidotes according to the invention.

The seeds of sorghum were treated with the antidotes in doses of 0.25 and 0.50 kg. antidote/kg. of seeds, by seed-dressing, and Lasso 48 EC was applied to the soil after seeding in a dose of 45 lit./ha.

Tests were performed on 10 m² plots, with four repetitions. Evaluation was made as described in the foregoing examples.

The results obtained are listed in the following Table 8.

TABLE 8

| Treatment | Dose (kg./q.) 0.25 green weight (%) | 0.50 |
|---|---|---|
| Lasso | 38 | 38 |
| N,N—diallyl-2,2-dichloroacetamide + Lasso | 90 | 95 |
| Compound No. 6 + Lasso | 95 | 100 |
| Compound No. 12 + Lasso | 92 | 100 |
| Compound No. 25 Lasso | 98 | 105 |
| Control (mechanical weed-killing) | 100 | 100 |

The results set forth in Table 8 clearly indicate that the injurious effect can practically entirely be eliminated by seed-dressing with the tested antidotes according to the invention, moreover, the green weight of sorghum treated with Compound No. 25 is higher than that of the sorghum collected from plots on which a mechanical weed-killing had been carried out.

The foregoing Examples 7 to 11 and Tables 2 to 8 unambiguously show that the tolerance of cultivated plants to known herbicides may be substantially increased, and in certain instances the injuries caused by known herbicides can be entirely eliminated by the use of dicarboxylic acid derivatives of the general formula I. The tests were carried out on four different cultivated plants and in combination with four different classes of herbicidal compounds, i.e. the useful effect of the antidote according to the invention is proved in a wide range, but we do not intend to limit our invention to the examples. Various modifications which are obvious for one skilled in the art of plant protection are also within the scope of the invention.

We claim:
1. Phthalic acid-bis-(2,2-dimethyl-1,3-oxazolidine).
2. Isophthalic acid-bis-(2,2-dimethyl-1,3-oxazolidine).
3. Terephthalic acid-bis(2,2-dimethyl-1,3-oxazolidine).
4. Terephthaloyl-2,2-dimethyl-1,3-oxazolidine.

* * * * *